US00PP29763P3

(12) United States Plant Patent
De Jong

(10) Patent No.: US PP29,763 P3
(45) Date of Patent: Oct. 16, 2018

(54) *SUTERA* PLANT NAMED 'SUTZ0006'

(50) Latin Name: *Sutera cordata*
Varietal Denomination: SUTZ0006

(71) Applicant: SYNGENTA PARTICIPATIONS AG, Basel (CH)

(72) Inventor: Erwin De Jong, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 145 days.

(21) Appl. No.: 14/999,987

(22) Filed: Jul. 22, 2016

(65) Prior Publication Data

US 2017/0135275 P1 May 11, 2017

Related U.S. Application Data

(60) Provisional application No. 62/253,161, filed on Nov. 10, 2015.

(51) Int. Cl.
*A01H 5/02* (2018.01)

(52) U.S. Cl.
USPC ..... Plt./485
CPC ..... *A01H 5/02* (2013.01)

(58) Field of Classification Search
USPC ..... Plt./485
See application file for complete search history.

*Primary Examiner* — Anne Marie Grunberg
(74) *Attorney, Agent, or Firm* — Dale Skalla

(57) ABSTRACT

A new *Sutera* plant named 'SUTZ0006' particularly distinguished by large, white flowers, medium to dark green foliage, medium to large sized, deltoid rounded leaves, good branching, mounding to semi trailing plant habit with improved floriferousness and continuous flowering.

1 Drawing Sheet

Figure 1:
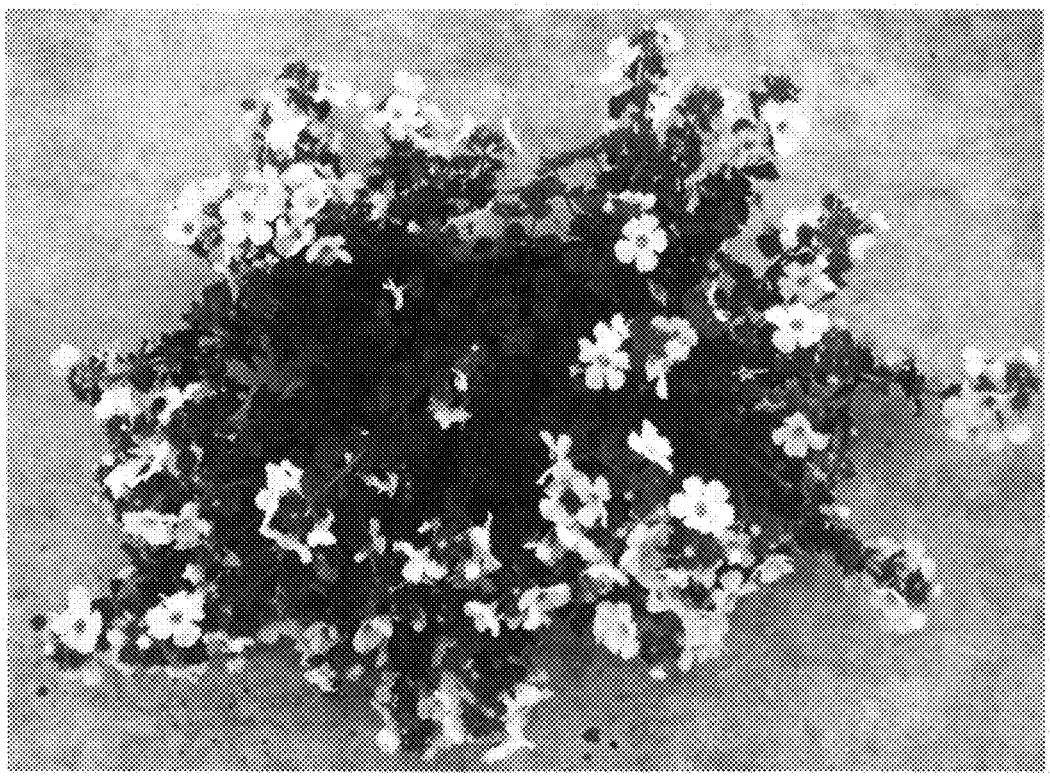
Figure 2:
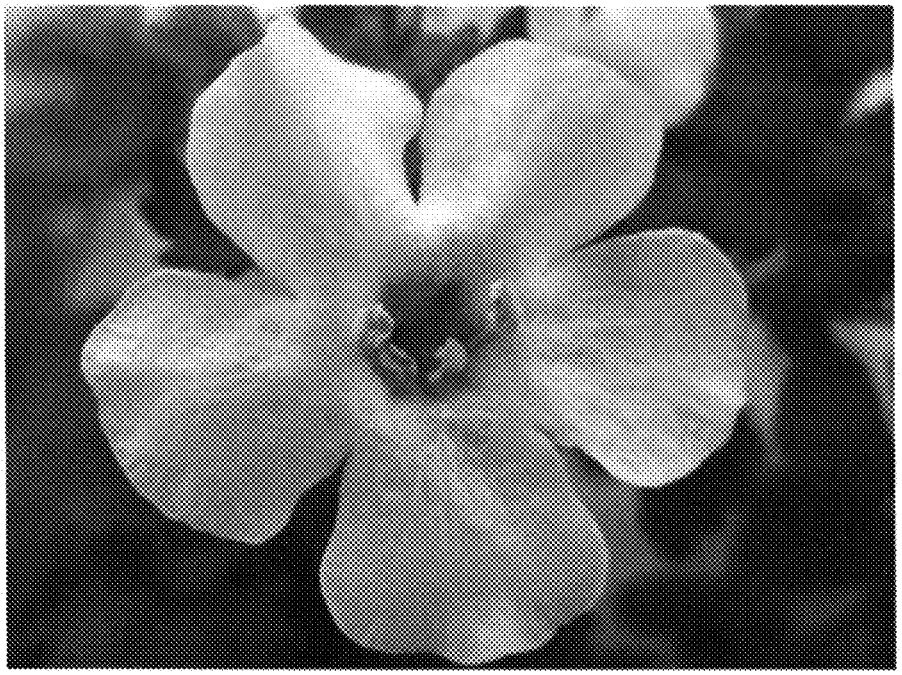

Latin name of the genus and species of the plant claimed: *Sutera cordata.*

Varietal denomination: 'SUTZ0006'.

BACKGROUND OF THE NEW PLANT

The present invention comprises a new *Sutera*, botanically known as *Sutera cordata*, and hereinafter referred to by the variety name 'SUTZ0006'.

'SUTZ0006' is a product of a planned breeding program. The improved cultivar has white, large sized flowers, medium to dark green foliage, mounded compact and semi-trailing plant habit with moderate to good branching. The cultivar is improved for floriferousness and continuous flowering.

'SUTZ0006' originated from a cross conducted during the summer of 2012 between a line designated 'M0014.1V' as the female parent which is taller and a line designated 'N0007.3V' as the male parent which has smaller flowers. The resultant seed was sown in a controlled breeding environment in the fall of 2012 in Enkhuizen, The Netherlands. In January 2013, 'SUTZ0006' was selected as one flowering plant within the progeny of the stated cross in summer 2012 in Enkhuizen, The Netherlands.

The first act of asexual reproduction of 'SUTZ0006' was accomplished when vegetative cuttings were propagated from the initial selection in February 2013 in a controlled environment in Enkhuizen, The Netherlands.

BRIEF SUMMARY OF INVENTION

Horticultural examination of plants grown from cuttings of the plant initiated in March 2013, and continuing thereafter, has demonstrated that the combination of characteristics as herein disclosed for 'SUTZ0006' are firmly fixed and are retained through successive generations of asexual reproduction.

'SUTZ0006' has not been observed under all possible environmental conditions. The phenotype may vary significantly with variations in environment such as temperature, light intensity and day length.

A Plant Breeder's Right for this cultivar has not yet been applied for. 'SUTZ0006' has not been made publicly available more than one year prior to the filing of this application.

The following traits have been repeatedly observed and are determined to be basic characteristics of the new variety. The combination of these characteristics distinguishes this *Sutera* as a new and distinct variety.

BRIEF SUMMARY OF THE INVENTION

The following observations, measurements, and comparisons describe plants grown indoors and outdoors in Andijk and Enkhuizen, The Netherlands, Sarrians, France and Gilroy, Calif. United States. The following traits have been repeatedly observed and are determined to be basic characteristics of the new variety. The combination of these characteristics distinguishes this *Sutera* as an improved and distinct variety:

1. 'SUTZ0006' is a white flowering *Sutera* with large flowers (diameter corolla is 2.5-3.0 cm).
2. Medium-dark green deltoid to round leaves.
3. Mounded semi trailing and a plant with improved floriferousness and continuous flowering.

COMPARISON WITH COMMERCIAL VARIETIES

'SUTZ0006' differs from the commercial *Sutera* cultivar Calypso Jumbo White, applied as 'SUTZ0001' (U.S. Plant Pat. No. 28,691) in that 'SUTZ0006' has bigger flowers, is more compact, more floriferous and is flowering continuously.

'SUTZ0006' differs from the commercial *Sutera* cultivar 'Gulliver Dynamic White' having U.S. Plant Pat. No. 23,147, in that 'SUTZ0006' has bigger flowers, is more floriferous and flowers more continuously.

BRIEF DESCRIPTION OF THE PHOTOGRAPHS

The accompanying photographic drawing shows typical flower and foliage characteristics of 'SUTZ0006' with colors being as true as possible with an illustration of this type.

The first and second photographic drawing shows a flowering potted plant of the new variety and a close-up of the flowers.

DETAILED BOTANICAL DESCRIPTION

The mentioned photographs were taken in October 2015 of a plant in 12 cm pot grown in a greenhouse in Enkhuizen, The Netherlands. The plants were 17 weeks old.

Color references are made to The Royal Horticultural Society Colour Chart (R.H.S.) 2001.

TABLE 1

DIFFERENCES BETWEEN THE NEW VARIETY 'SUTZ0006' and 'SUTZ0001' (measurements based on approximately 17 weeks old plants in 12 cm pot, October 2015)

| Traits: | 'SUTZ0006' | 'SUTZ0001' |
|---|---|---|
| Flower diameter: | 2.5-3.0 cm | 2.6 cm |
| Branching (amount of branches per plant): | 85-90 (main + big side branches) | 85-95 (main + big side branches) |
| Length main shoot: | 22-30 cm | 42-47 cm |
| Floriferousness (estimated # open flowers per plant: | 150 | 135 |

Plant:

*Growth and habit.*—Slightly compact, semi trailing, mounded, well branched plant with shorter internodes than 'SUTZ0001'.

*Height.*—8-11 cm (above soil).

*Width (diameter).*—42-60 cm, including flowers.

*Spread (including flowers).*—1 main branch in 12 cm pot measures 28-30 cm length.

*Number of branches.*—85-90 (main+big side branches).

*Time to produce a finished flowering plant.*—11-12 weeks for 12 cm pot.

*Outdoor plant performance.*—Used for hanging baskets, mixed container plantings, is floriferous and continuous flowering.

*Time to initiate and develop roots.*—21 days at 19-22° C.

*Root description.*—Fine, fibrous and freely branching.

Stem:

*Characteristics.*—Cross section round, fair degree of self-branching.

*Stem length.*—22-24 cm.

*Diameter.*—2 mm.

*Internode length.*—1-3 cm.

*Color.*—RHS 140A, no anthocyanin.

*Texture.*—Pubescent/Canescent.

Foliage:

*Arrangement.*—Opposite, decussate.

*Leaf shape.*—Initially deltoid, later nearly round.

*Apex.*—Acute.

*Base.*—Rhomboidal.

*Margin.*—Serrate.

*Leaf length.*—1.5-2.0 cm.

*Leaf width.*—1.5-2.5 cm.

*Immature leaf, color upper surface.*—RHS N134B.

*Immature leaf, color lower surface.*—RHS N134D.

*Mature color upper surface.*—RHS N134B.

*Mature color lower surface.*—RHS N134D.

*Venation type.*—Palmate.

*Venation color.*—RHS 134B.

*Texture.*—Both surfaces have a bit of puberulous texture.

Petiole:

*Length.*—0.4 cm.

*Petiole width.*—Up to 2 mm.

*Petiole color.*—RHS N134B.

*Texture.*—Pubescent.

Inflorescence:

*Blooming habit.*—When temperatures exceed 25 degrees C. it will keep on flowering through the growing season from spring to fall. 'SUTZ0006' has some improved heat tolerance.

*Type of inflorescence.*—Solitary, flowers emerge from the leaf axils of the upper stem nodes, usually 2 flowers per node.

*Quantity of flowers per stem.*—About 8-10 flowers and additional buds in a cluster at the end of the stem.

*Fragrance.*—None.

Pedicel:

*Color.*—RHS 134A.

*Length.*—0.6-0.8 cm.

*Diameter.*—0.1 cm.

*Texture.*—Dense pubescence.

Flower:

*Corolla type and shape.*—Single-type, nearly round, lower part funnel-shaped formed by 5, mainly fused petals. Upper part is salver-shaped formed by the almost free petal lobes.

*Corolla diameter.*—2.5-3.0 cm.

*Flower length.*—About 1.0-1.4 cm.

*Funnel diameter.*—0.5-0.6 cm.

*Color upper surface.*—Whiter than RHS N155B.

*Color lower surface.*—Whiter than RHS N155B.

*Color of throat.*—Deep yellow to orange, RHS 23A.

*Color of funnel outer side.*—RHS 17B.

Petal (lobes):

*Apex.*—Rounded to obovate.

*Base.*—Fused.

*Margin.*—Entire.

*Texture.*—Upper side is smooth glabrous and a bit puberulous in the throat. Under side glabrous to very short pubescence, increasing on the corolla tube.

*Length of lobes, (from the corolla opening).*—1.2 cm.

*Width of lobes.*—10-12 mm.

Flower bud:

*Shape.*—Cone-shaped.

*Diameter.*—0.5-0.8 cm.

*Length.*—0.7-1.0 cm.

*Color (at tight bud).*—Greenish-white, RHS 150D.

Calyx:

*Shape*.—5 sepals in a whorl around the flower base.

*Sepal shape*.—Lanceolate, fused at the base.

*Sepal color*.—RHS 137C.

*Length*.—0.5-0.6 cm.

*Width*.—About 1 mm.

*Apex*.—Acuminate.

*Base*.—Fused.

*Texture*.—Covered with dense hair.

Reproductive organs:

Stamens:

*Quantity*.—4.

*Filament, color*.—White, RHS N155B.

*Length*.—1.2-1.4 cm.

*Diameter*.—0.1 cm.

*Anther color*.—Yellow, RHS 12A.

*Pollen amount*.—Moderate.

*Pollen color*.—Yellow, RHS 12A.

Pistil:

*Quantity per flower*.—One.

*Length*.—1.1-1.3 cm.

*Stigma color*.—Light green, RHS N144D.

*Style color*.—Greenish white, RHS 144D.

Fruit and seed set: Has not been observed.

Disease and insect resistance: Resistance and susceptibility typical for the species, no special observations made.

What is claimed is:

1. A new and distinct cultivar of *Sutera* plant named 'SUTZ0006' plant substantially as illustrated and described herein.

* * * * *